(12) United States Patent
Vos et al.

(10) Patent No.: US 10,773,957 B2
(45) Date of Patent: Sep. 15, 2020

(54) METHOD FOR RECOVERING HCl FROM A HCl CONTAINING GAS STREAM

(71) Applicant: NOURYON CHEMICALS INTERNATIONAL B.V., Arnhem (NL)

(72) Inventors: Hendrik Jan Vos, Apeldoorn (NL); Lars Magnus Tollin, Skoghall (SE); Cornelis Kooijman, Deventer (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 389 days.

(21) Appl. No.: 15/560,400

(22) PCT Filed: Mar. 25, 2016

(86) PCT No.: PCT/EP2016/056688
§ 371 (c)(1),
(2) Date: Sep. 21, 2017

(87) PCT Pub. No.: WO2016/156257
PCT Pub. Date: Oct. 6, 2016

(65) Prior Publication Data
US 2018/0057358 A1    Mar. 1, 2018

(30) Foreign Application Priority Data
Mar. 30, 2015    (EP) .................................... 15161666

(51) Int. Cl.
*C01B 7/07* (2006.01)
*B01D 53/14* (2006.01)
(Continued)

(52) U.S. Cl.
CPC ........ *C01B 7/0706* (2013.01); *B01D 53/1406* (2013.01); *B01D 53/1456* (2013.01);
(Continued)

(58) Field of Classification Search
CPC ...... B01D 2258/0266; B01D 2311/103; B01D 2313/23; B01D 53/228; B01D 53/268;
(Continued)

(56) References Cited

U.S. PATENT DOCUMENTS 3,658,483 A    4/1972  Lienau et al.
3,807,139 A    4/1974  Di Fiore et al.
(Continued)

FOREIGN PATENT DOCUMENTS

CN    101 190 396 A    6/2008
CN    101 823 694 A    9/2010
(Continued)

OTHER PUBLICATIONS

Severin et al., "Hydrochloric Acid", Ullmann's Encyclopedia of Industrial Chemistry, 2000, vol. 18, 191-205.
(Continued)

*Primary Examiner* — Sharon Pregler
(74) *Attorney, Agent, or Firm* — Lorenz & Kopf, LLP

(57) ABSTRACT

The invention pertains to a method for recovering HCl from a HCl containing gas stream wherein a HCl containing gas stream with a temperature of −20 to 25° C. is provided to an adiabatic absorption unit where it is contacted with water as an absorbent, resulting in the formation of a top gas stream and a aqueous HCl product solution, wherein the temperature of the top gas stream is at least 70° C. and wherein the aqueous HCl product solution has a HCl concentration in the range of 5-20 wt. %. It is preferred for the HCl-containing gas stream to be derived from a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA. The HCl product solution is preferably diluted to a concentration of 1-8 wt. %,
(Continued)

and the diluted solution is used as absorbent in a second absorption step, wherein HCl is absorbed from a further HCl-containing gas stream to form a second aqueous HCl solution. The further HCl-containing gas stream is preferably derived from a chlorination step wherein acetic acid is reacted with chlorine, resulting in the formation of the further HCl-containing gas stream and a feed comprising monochloroacetic acid (MCA) and dichloroacetic acid (DCA).

15 Claims, 2 Drawing Sheets

(51) Int. Cl.
*C07C 51/487* (2006.01)
*B01D 53/68* (2006.01)
*C07C 51/377* (2006.01)
*C07C 7/00* (2006.01)

(52) U.S. Cl.
CPC ......... *B01D 53/1493* (2013.01); *B01D 53/68* (2013.01); *C07C 51/377* (2013.01); *C07C 51/487* (2013.01); *B01D 2252/103* (2013.01); *B01D 2257/2045* (2013.01)

(58) Field of Classification Search
CPC .... B01D 63/06; B01D 71/021; B01D 71/024; B01D 71/06
See application file for complete search history.

(56) References Cited

U.S. PATENT DOCUMENTS

| | | | |
|---|---|---|---|
| 4,003,723 A | | 1/1977 | Schafer et al. |
| 4,488,884 A | * | 12/1984 | Parigi ........................ C01B 7/01 423/488 |
| 2010/0029984 A1 | | 2/2010 | Timmermans et al. |

FOREIGN PATENT DOCUMENTS

| | | |
|---|---|---|
| CN | 102 249 189 A | 11/2011 |
| CN | 104 258 690 A | 1/2015 |
| EP | 0 618 170 A1 | 10/1994 |
| FR | 1 313 784 A | 1/1963 |
| GB | 1 032 806 A | 6/1966 |
| JP | 48-62693 A | 9/1973 |
| JP | 52-36999 B1 | 9/1977 |
| JP | 63-50303 A | 3/1988 |
| PL | 167441 B1 | 9/1995 |

OTHER PUBLICATIONS

"Chloressigsauren", Ullmann's Encyklopadie der technischen Chemie, 3rd edition, vol. 5, 390-391.

* cited by examiner

METHOD FOR RECOVERING HCl FROM A HCl CONTAINING GAS STREAM

This application is the US national phase under 35 U.S.C. § 371 of international application PCT/EP2016/056688, filed Mar. 25, 2016, which claims priority to European application EP 15161666.1, filed Mar. 30, 2015.

The present invention pertains to a method for recovering HCl from a HCl-containing gas stream. The invention pertains in particular to the recovery of HCl from gas streams containing organic contaminants, and in particular gas streams origination from the manufacture of monochloroacetic acid.

Chloroacetic acids can be obtained by reacting acetic acid with chlorine in a chlorination step, resulting in the formation of a chloroacetic acid stream and HCl as side product. Acetic anhydride is often added as catalyst. The resulting chloroacetic acid stream generally comprises a mixture of the desired product monochloroacetic acid (MCA) with "overchlorinated" products like dichloroacetic acid (DCA) and trichloroacetic acid (TCA). In particular, DCA may be present in the reaction product mixture in an amount of up to 6 wt. %. To convert these "overchlorinated" products to MCA, the product of the chlorination reaction is often subjected to a hydrogenation step, in which the DCA and other overchlorinated compounds are converted to MCA. This results in the formation of a product stream comprising MCA and a further side product stream comprising HCl.

In the overall reaction, the formation of one mole MCA from acetic acid is accompanied by the formation of one mole of HCl. The overchlorination followed by additional hydrogenation results in the formation of further HCl. Therefore, the manufacture of MCA is accompanied by the formation of large HCl streams.

CN104258690 describes a method for processing the HCl containing gas streams generated in a process for manufacturing MCA are processed by passing a HCl tail gas stream from the hydrogenation step to an absorber, and using a dilute aqueous HCl solution derived therefrom as absorbent in absorbing HCl from a tail gas derived from the chlorination unit.

There is need in the art for a method for recovering HCl from a HCl-containing gas stream, e.g. generated in a process for manufacturing MCA, which allows efficient separation of HCl from other components of the gas stream, which process is attractive from a technical, environmental, and economic point of view. The present invention provides such a method.

The present invention pertains to a method for recovering HCl from a HCl containing gas stream wherein a HCl containing gas stream with a temperature of −20 to 25° C. is provided to an adiabatic absorption unit where it is contacted with water as an absorbent, resulting in the formation of a top gas stream and an aqueous HCl product solution, wherein the temperature of the top gas stream is at least 70° C. and wherein the aqueous HCl product solution has a HCl concentration in the range of 5 to 20 wt. %.

It has been found that a method as specified above makes it possible to effectively remove HCl from a HCl-containing gas stream, while organic contaminants in the HCl-containing gas stream are not absorbed, but can be processed separately. Further advantages of the process according to the invention and specific embodiments thereof will become clear from the further specification.

It is noted that absorption is the process in which a fluid is dissolved by a liquid or a solid (absorbent). Adsorption is the process in which atoms, ions or molecules from a substance (it could be gas, liquid or dissolved solid) adhere to a surface of the adsorbent. Accordingly, the term adsorption should be used in case of a surface-based process where a film of adsorbate is created on the surface while the term absorption should be used in case of absorption into the entire volume of the absorbing substance. It is clear that there is a distinction between the two. Nevertheless, in the art, the terms absorption and adsorption are often used as alternatives for one another. Whether a process should officially have to be denoted as an adsorption process or as an absorption process, is not so relevant as it becomes clear from the process itself whether or not a film or adsorbate is created on the surface of a substance (i.e. adsorption) or whether absorption takes place into the entire volume of a substance (i.e. absorption). The presently claimed process should officially be denoted as an absorption process.

U.S. Pat. No. 4,488,884 relates to a process for continuously producing aqueous hydrochloric acid having a concentration of at least 35.5% by weight. More particularly, it describes a process for continuously producing aqueous hydrochloric acid having a concentration of at least 35.5% by weight comprising (a) continuously introducing water to the top of an absorption unit, (b) continuously introducing a gas stream containing anhydrous hydrogen chloride to the bottom of said absorption unit, (c) removing an overhead gaseous stream from said unit, said gaseous stream containing no more than 3% by weight, and preferably no more than 1% by weight hydrogen chloride, and (d) removing a bottom liquid stream from said unit, said bottom stream containing at least 35.5% by weight hydrogen chloride, and (e) returning a portion of said bottom stream to said unit. The temperature inside the absorption unit follow the hydrogen chloride concentration boiling point curve and therefore range from 55° C. at the bottom of the unit to a high temperature of 108° C. at the location in the unit where the acid concentration is 22% by weight. The top of the column operates between 95 and 100° C. The temperature of the gas stream is generally between 0 and 30° C. In order to produce an overhead gaseous stream containing at most 3% by weight of hydrogen chloride, said gaseous stream is cooled in a heat exchanger supplied with cooling water.

The process according to the invention differs from the process described herein at least in that the hydrogen chloride concentration in the HCl product solution is much lower than that specified in this reference.

It is noted that PL167441 describes absorbing HCl from a HCl containing gas stream, with encompasses dividing a gas containing at least 40 mole % HCl and at most 20 mole % of organo-chloro contaminants and $SO_2$ into two streams which are provided to an adiabatic absorber. The first stream has a temperature of 50-110° C. and is fed to a 65-110° C. absorber zone. The second stream has a temperature of 20-80° C. and is fed to a 50-85° C. absorber zone. An aqueous solution with a HCl concentration of 3-25 wt. % is used as absorbent. The process according to the invention differs from the process described herein at least in that the entry temperature of the HCl stream is much lower than that specified in this reference.

The process will be discussed in more detail below, with reference to the following figures, without being limited thereto or thereby.

Figure 1:
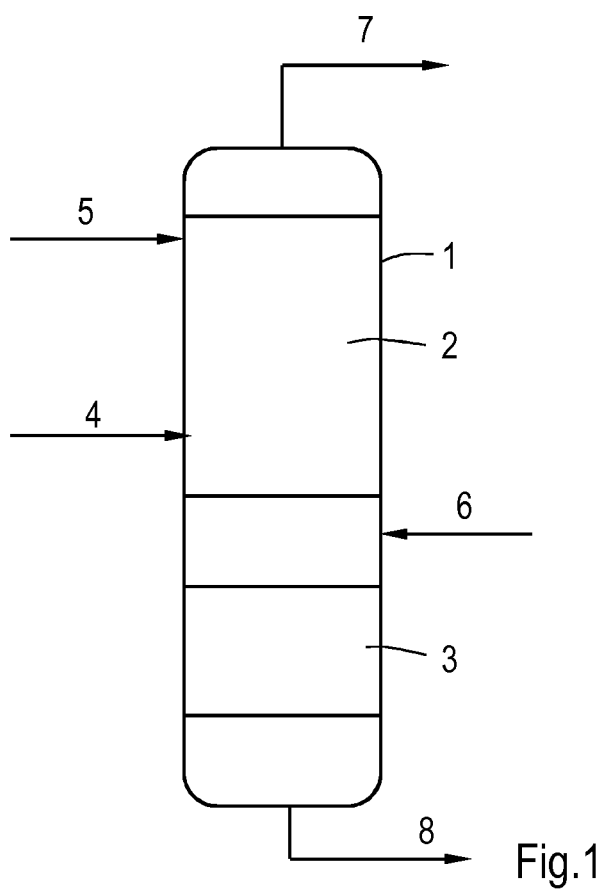
FIG. 1 illustrates a first embodiment of the present invention.

In FIG. 1, (1) is the adiabatic absorption unit, having an absorption section (2) and a cooling section (3). The HCl-containing gas is provided through line (4). Absorbent water is provided through line (5). Steam can be provided through line (6). The top gas stream is withdrawn through line (7). The aqueous HCl product solution is withdrawn through line (8).

In the method according to the invention a HCl containing gas stream with a temperature of −20 to 25° C. is provided to an adiabatic absorption unit. The HCl-containing gas stream generally comprises between 10 and 90 vol % HCl, in particular between 20 and 80 vol %.

The HCl-containing gas stream may comprise organic compounds, in particular when it is derived from a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA. In one embodiment, the HCl-containing gas steam comprises one or more of the following organic compounds, in the following amounts:

acetic acid: less than 1 wt. %, preferably less than 0.5 wt. %, in some embodiments more preferably less than 0.05 wt. %, and if present generally in an amount of at least 1 ppm, but mostly in an amount of at least 50 mg/kg.

acetaldehyde: less than 1 wt. %, preferably less than 0.5 wt. %, in some embodiments less than 0.3 wt. %, and if present generally in an amount of at least 1 ppm, but mostly in an amount of at least 500 mg/kg.

total of chlorinated acids and chlorinated aldehydes: less than 1 wt. %, preferably less than 0.5 wt. %, in some embodiments less than 0.1 wt. %, and if present generally in an amount of at least 1 ppm, but mostly in an amount of at least 50 mg/kg.

The temperature of the HCl-containing gas stream which is provided to the adiabatic absorption unit is in the range of −20 to 25° C. It has been found that this temperature range makes it possible to obtain a process which results in a high yield of HCl and low amounts of organic contaminants in the aqueous HCl product solution. It may be preferred for the temperature of the HCl-containing gas stream to be in the range of −5 to 20° C., more preferably, 0 to 20° C., still more preferably 10 to 15° C.

In the adiabatic absorption unit, the HCl-containing gas stream is contacted with water which serves as an absorbent for the HCl. The amount of water is selected such that the resulting aqueous HCl solution has a HCl concentration in the range of 5-20 wt. %, in particular 10-20 wt. %, more in particular in the range of 13-18 wt. %. The water provided to the adiabatic absorption unit generally has a temperature in the range of 10 to 50° C., in particular 20 to 40° C.

The water provided to the adiabatic absorption unit may comprise limited amounts of further compounds, as is conventional for water streams used in commercial industrial operation, but it comprises at least 97 wt % water, more preferably at least 98 wt % water, and most preferably at least 98.5 wt % water.

The absorbent, i.e. water, provided to the unit generally has a HCl concentration of below 1 wt. %, in particular below 0.5 wt. %, because higher HCl concentrations will detrimentally affect the capacity of the water to take up HCl from the HCl-containing gas stream. Moreover, higher HCl concentrations will give less heat of absorption, leading to a lower temperature of the top gas stream.

In a preferred embodiment, the water enters the absorption unit above the location where the HCl enters the absorption unit. This is because it ensures a better contact between the water, which travels down in the unit and the gas stream, which travels upwards in the unit.

A key feature of the process according to the invention is that the temperature of the top gas stream withdrawn from the unit is at least 70° C. It has been found that by selecting this temperature, organic contaminants present in the HCl-containing gas stream are not absorbed into the HCl solution but are removed with the top gas stream. It may be preferred for the temperature of the top gas stream to be at least 77° C., more preferably at least 83° C., in particular at least 87° C., in some embodiments at least 94° C., to increase the removal of aldehydes, in particular acetaldehyde and chloroacetaldehyde, with the top stream.

It has been found that it is preferred for the temperature of the top gas stream to be at most 95° C., preferably at most 93° C., and most preferably at most 90° C.

This is because at higher temperatures the loss of HCl over the top of the unit increases, resulting in a decrease in the yield of HCl.

In a preferred embodiment, steam is added to the adiabatic absorption column. The addition of steam has been found advantageous to ensure that the top temperature is in the range specified above. It may be preferred for the steam to have a temperature of 100-200° C., at a pressure of above 1 to 12 bar (absolute), more preferably 1 to 4 bar (absolute), still more preferably 1 to 2 bar (absolute). The steam is preferably added to the absorption unit at a point below the entry point of the HCl-containing gas stream. The amount of steam is selected such that the above mentioned temperature range is obtained.

For all streams provided to the unit, i.e., water, HCl gas, and optionally steam, it is possible to add them at a single point in the column. Multiple point addition is also possible.

The top gas stream, withdrawn from the unit preferably has a HCl concentration of less than 5 wt. %, in particular less than 3 wt %, more particular less than 1 wt. %. Depending on the composition of the HCl-containing gas stream used as starting material in the process according to the invention may contain organic contaminants. It is a feature of the present invention that the absorption process allows separation of the organic compounds from the aqueous HCl product stream. It is therefore preferred that of the organic contaminants present in the starting HCl-containing gas stream at least 30 wt. % ends up in the top gas stream and are therewith removed, in particular at least 50 wt. %, more in particular at least 80 wt. %, in some embodiments at least 90 wt. %. The percentages removed and the absolute concentrations are dependent on the amount and type of organic contaminants in the starting gas stream.

It is noted that in the process according to the present invention, it is not needed to cool the top gas stream using e.g. a heat exchanger.

The aqueous HCl solution withdrawn from the adiabatic absorption unit has a HCl concentration in the range of 5-20 wt. %, in particular 10-20 wt. %, more in particular in the range of 13-18 wt. %. It is preferred for the HCl solution to contain less than 0.5 wt. % or organic contaminants, in particular less than 0.1 wt. %.

In one embodiment, a cooler is present at the bottom end of the adiabatic absorption unit, which cools the aqueous HCl solution to a temperature below 60° C., in particular below 50° C. The cooler can, e.g., be in the form of a falling film cooler.

It is noted that in the process of the present invention, preferably no substantial portion of said aqueous HCl solution (i.e. less than 5 wt % thereof) is returned to the adiabatic absorption unit, and most preferably, the aqueous HCl solution is not recycled to the adiabatic absorption unit at all.

The process according to the invention find particular application in the processing of HCl containing gas streams which are formed in the production of MCA from acetic acid and chlorine, in particular to HCl-containing gas streams which are derived from a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA.

In other words, in a preferred embodiment the HCl containing gas stream is obtained as a by-product stream of a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA.

Hydrogenation of a feed comprising monochloroacetic acid (MCA) and dichloroacetic acid (DCA) by reaction with hydrogen to form a HCl-containing gas stream and a product stream comprising MCA and a reduced amount of DCA is known in the art, and requires no further elucidation here. In general, a feed comprising MCA and between 2 and 6 wt. % DCA is contacted with hydrogen gas in the presence of a catalyst to form a product comprising MCA and an amount of DCA which is lower than the amount of DCA present in the feed, e.g., in the range of 0-0.8 wt. %.

The hydrogenation step can, for example, be carried out in a vertical tubular reactor containing a solid heterogeneous hydrogenation catalyst fixed bed. The heterogeneous hydrogenation catalyst according to the present invention preferably comprises between 0.1 and 3% by weight, more preferably between 0.5 and 2% by weight, based on the total weight of the heterogeneous catalyst, of one or more metals of Group VIII of the Periodic Table of the Elements. The temperature in the top of the reactor is preferably kept between 100 and 200° C., and more preferably between 145 and 175° C. The pressure in the top of the vertical tubular reactor is preferably kept between 0.2 and 1.0 MPa, preferably between 0.3 and 0.6 MPa.

The HCl-containing gas stream as produced in the hydrogenation step can be provided directly to the adiabatic absorption step. It is also possible for the HCl-containing gas stream as produced in the hydrogenation step to be provided indirectly to the adiabatic absorption step, i.e. after it has been subjected to one or more intermediate processing steps. For example, it is preferred for the HCl-containing gas stream as produced in the hydrogenation step to be first subjected to a cooling step, e.g., to a temperature in the range of −20 to 25° C. This step results in a decrease in the organic contaminant content in the HCl containing gas stream.

In other words, in one embodiment of the present invention the HCl-containing gas stream is derived directly from a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA. In another embodiment of the present invention the HCl-containing gas stream is indirectly derived from a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA, with the HCl-containing gas stream as produced in the hydrogenation step being subjected to one or more intermediate steps, e.g., a cooling step, between the hydrogenation step and the absorption step.

The top gas stream and the aqueous HCl product stream produced by the method according to the invention can be processed as desired. Depending on its composition, the top gas stream can e.g. be vented off. However, if the top gas stream comprises significant amounts of organic contaminants, they will generally be removed and recycled, e.g., to the manufacture of MCA or discharged with the waste water to a biological waste water treatment plant.

The aqueous HCl product stream can be processed as desired. It can be used in one or more of the many processes where aqueous HCl solutions are used.

In a particular embodiment of the process according to the invention, the HCl product solution is diluted to a concentration of 1-8 wt. %, and the diluted solution is used as absorbent in a second absorption step, wherein HCl is absorbed from a further HCl-containing gas stream to form a second aqueous HCl solution.

In one embodiment, the second absorption step is carried out under isothermal conditions and/or at a temperature in the range of 20-60° C., preferably under isothermal conditions at a temperature in the range of 20-60° C.

The further HCl containing gas stream provided to the second absorption step generally comprises between 98 and 100 vol % HCl, more in particular between 99.5 and 100 vol %.

The further HCl-containing gas stream may comprises organic compounds, in particular when, as in a preferred embodiment of the invention, it is derived from a chlorination step wherein acetic acid is reacted with chlorine, resulting in the formation of the further HCl-containing gas stream and a feed comprising monochloroacetic acid (MCA) and dichloroacetic acid (DCA). In this case, the HCl-containing gas steam generally comprises the following organic impurities in the following amounts:

acetic acid: lower than 1 wt. %, preferably lower than 0.1 wt. %, sum of monochloro acetic acid, acetaldehyde, chloroacetaldehyde and dicloroacetaldhyde: lower than 1 wt. %, preferably lower than 0.1 wt. %.

The gas stream withdrawn from the second absorption step mainly contains HCl. In principle, the volume of this stream is kept to a minimum because the intention is that the HCl is absorbed into the absorbent liquid. Depending on the composition of the HCl-containing gas stream used as starting material in the process according to the invention it may contain some organic contaminants.

In one embodiment, the second HCl solution produced by the second absorption step has a HCl concentration in the range of 25-34 wt. %, in particular 30-34 wt. %. This can be regulated by selecting the amount and concentration of the diluted HCl solution and the amount and concentration of the further HCl-containing gas stream.

It is preferred for the second HCl solution to have a concentration of organic contaminants of less than 0.5 wt. %, in particular less 0.05 wt. %.

As indicated above, it is particularly preferred for the further HCl-containing gas stream to be obtained as a by-product of a chlorination step wherein acetic acid is reacted with chlorine, resulting in the formation of the further HCl-containing gas stream and a feed comprising monochloroacetic acid (MCA) and dichloroacetic acid (DCA). This makes for an integrated process wherein both the HCl-containing gas stream derived from the hydrogenation step in the manufacture of MCA and the HCl-containing gas stream derived from the chlorination step are processed in an integrated manner.

Chlorination of acetic acid by reaction thereof with chlorine resulting in the formation of a HCl-containing gas stream and a feed comprising monochloroacetic acid (MCA) and dichloroacetic acid (DCA) is known in the art, and requires no further elucidation here. Such a process is commonly known and generally makes use of a reactor in which a mixture of liquid acetic acid (HAc) is reacted with chlorine under anhydrous conditions, using acetyl chloride as the catalyst. Acetyl chloride is preferably formed in-situ by the addition of e.g. acetic anhydride. The chlorination pressure is generally is 0.3-0.6 MPa and temperature generally is 120-160° C.

The HCl-containing gas stream as produced in the chlorination step can be provided directly to the second absorption step. It is also possible for the HCl-containing gas stream as produced in the chlorination step to be provided indirectly to the second absorption step, i.e. after it has been subjected to one or more intermediate processing steps. For example, it is preferred for the HCl-containing gas stream as produced in the chlorination step to be first subjected to a cooling step, e.g., to a temperature in the range of −20 to 60° C. This cooling step may result in a decrease in the organic contaminant content in the HCl containing gas stream.

Thus, in one embodiment of the present invention the HCl-containing gas stream is derived directly from a chlorination step wherein acetic acid is reacted with chlorine, resulting in the formation of the further HCl-containing gas stream and a feed comprising monochloroacetic acid (MCA) and dichloroacetic acid (DCA). In another embodiment of the present invention the HCl-containing gas stream is indirectly derived from a chlorination step wherein acetic acid is reacted with chlorine, resulting in the formation of the further HCl-containing gas stream and a feed comprising monochloroacetic acid (MCA) and dichloroacetic acid (DCA), with the HCl-containing gas stream as produced in the chlorination step being subjected to one or more intermediate steps, e.g., a cooling step between the chlorination step and the absorption step.

In one embodiment, the present invention pertains to a method for recovering HCl from a HCl containing gas stream comprising the steps of providing a HCl containing gas stream with a temperature of −20 to 25° C., which is obtained as a by-product of a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA, feeding the HCl containing gas stream to an adiabatic absorption unit where it is contacted with water as an absorbent, resulting in the formation of a top gas stream and a aqueous HCl product solution, wherein the temperature of the top gas stream is at least 70° C. and wherein the aqueous HCl product solution has a HCl concentration in the range of 5-20 wt. %, diluting the aqueous HCl product solution to a concentration 1-8 wt. %, and providing the diluted solution as absorbent in a second absorption step, wherein HCl is absorbed from a further HCl-containing gas stream to form a second aqueous HCl solution, which further HCl-containing gas stream is obtained as a by-product of a chlorination step wherein acetic acid is reacted with chlorine resulting in the formation of the second HCl-containing gas stream and a feed comprising monochloroacetic acid (MCA) and dichloroacetic acid (DCA).

The preferred embodiments for the various aspects of the present invention, e.g., the absorption steps, as discussed above also apply to this integrated process.

Figure 2:
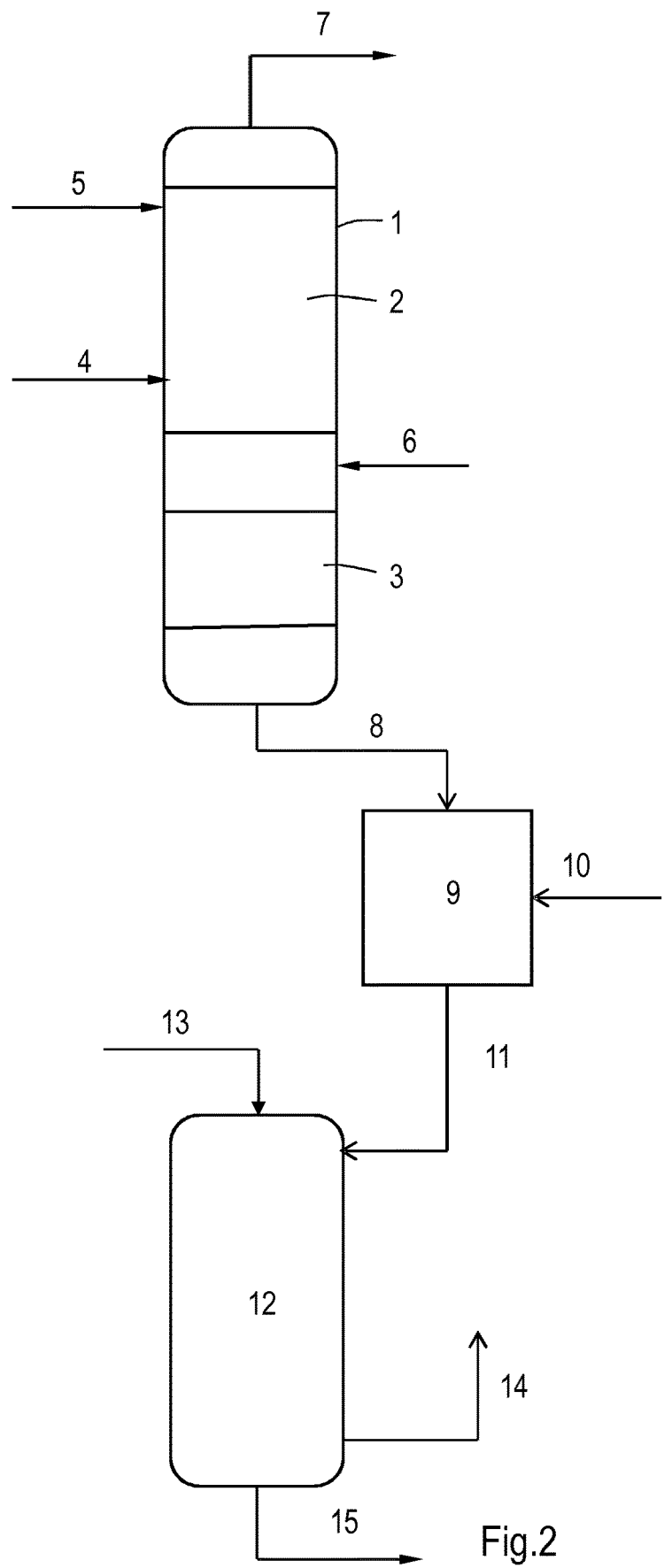
FIG. 2 illustrates a second embodiment of the present invention.

FIG. 2 shows a preferred embodiment of the method according to the invention, without being limited thereto or thereby.

In FIG. 2, (1) is the adiabatic absorption unit, having an absorption section (2) and a cooling section (3). The HCl-containing gas is provided through line (4). It has a temperature in the range of −20 to 25° C. and preferably is derived from a hydrogenation step (not shown) wherein a feed comprising monochloroacetic acid (MCA) and dichloroacetic acid (DCA) is reacted with hydrogen to form a HCl-containing gas stream and a product stream comprising MCA and a reduced amount of DCA, either directly, or after one or more intermediate steps such as a cooling step. Absorbent water is provided through line (5). Steam can be provided through line (6). The top gas stream is withdrawn through line (7). The aqueous HCl product solution is withdrawn through line (8). The aqueous HCl product solution, which has a HCl concentration in the range of 5-20 wt. %, preferably 10-20 wt. %, in particular in the range of 13-18 wt. %, is provided to a dilution unit (9), where water is added through line (10), to form a diluted solution with a concentration in the range of 1-8 wt. %, which is withdrawn through line (11), and provided to a second absorption unit (12). In absorption unit (12) the diluted solution is used as absorbent to absorb HCl from a further HCl-containing gas stream, which is provided to absorption unit (12) through line (13). A top off gas stream is withdrawn through line (14), and an aqueous HCl solution is withdrawn through line (15). Preferably, the further HCl containing gas stream is derived from a chlorination step (not shown) wherein acetic acid is reacted with chlorine, resulting in the formation of the further HCl-containing gas stream and a feed comprising monochloroacetic acid (MCA) and dichloroacetic acid (DCA), either directly, or after one or more intermediate steps such as cooling.

It will be clear to the skilled person that the various embodiments and preferences described herein can be combined, unless they are presented as mutually excluding alternatives.

The present invention will be elucidated by the following example, without being limited thereto or thereby.

EXAMPLE 1

A HCl starting gas was provided with a HCl concentration of 50 vol. %. The gas comprised about 5000 ppm of acetaldehyde, and minor amounts of other contaminants. The HCl gas was derived from a hydrogenation step wherein a feed comprising monochloroacetic acid (MCA) and dichloroacetic acid (DCA) was reacted with hydrogen to form a HCl-containing gas stream and a product stream comprising MCA and a reduced amount of DCA, followed by an intermediate cooling step.

The HCl-containing gas stream was provided to an adiabatic absorption unit at a temperature of 17° C. Water was provided to the absorption unit at a location above the entrance point of the HCl-containing gas stream. The water had a temperature of 35° C. The amount of water was selected such that the resulting HCl solution had a concentration of 16 wt. %. Steam was provided to the unit at an entrance point below that of the HCl-containing gas stream. The steam was provided at a temperature of 150° C. Compared to the amount of water, a small amount of steam is added to increase the temperature of the top gas stream to 90° C.

The HCl-containing aqueous solution produced in the adiabatic absorption unit passed down from the absorption unit into a cooler, and was withdrawn from the cooler at a temperature of 40° C. Of the acetaldehyde present in the HCl starting gas stream, more than 80% ended up in the gas stream removed from the adiabatic absorption unit.

The aqueous HCl product solution was diluted to a HCl-concentration of 3 wt. % and provided to an isothermal absorption unit where it was used to absorb HCl from a further HCl containing gas stream. The gas stream was derived from a chlorination step wherein acetic acid is reacted with chlorine resulting in the formation of the second HCl-containing gas stream and a feed comprising acetic acid (HAc) and monochloroacetic acid (MCA), after cooling. The absorption step was carried out under isothermal conditions at a temperature of 40° C. The absorption step yielded an aqueous HCl product solution with an HCl concentration of 30 wt. %.

The invention claimed is:

1. A method for recovering HCl from a HCl containing gas stream, the method comprising
    providing a HCl containing gas stream with a temperature of −20 to 25° C. to an adiabatic absorption unit where it is contacted with water as an absorbent, resulting in the formation of a top gas stream and an aqueous HCl product solution,
    providing steam to the adiabatic absorption unit to maintain the temperature of the top gas stream to be at least 70° C. and at most 95° C. and wherein the amount of water is selected such that the aqueous HCl product solution has a HCl concentration in the range of 5-20 wt. %.

2. The method according to claim 1, wherein the absorbent provided to the unit generally has a HCl concentration of below 1 wt. %.

3. The method according to claim 1, wherein the HCl-containing gas stream is obtained as a by-product of a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA.

4. The method according to claim 1, wherein steam is added to the adiabatic absorption unit at a pressure of above 1 to 12 bar (absolute).

5. The method according to claim 1, wherein the top gas stream has a temperature of at least 77° C.

6. The method according to claim 1, wherein the temperature of the HCl-containing gas stream provided to the absorption unit is in the range of −5 to 20° C.

7. The method according to claim 1, wherein the aqueous HCl product solution has a HCl concentration in the range of 10-20 wt. %.

8. The method according to claim 1, wherein the HCl product solution is diluted to a concentration of 1-8 wt. %, and the diluted solution is used as absorbent in a second absorption step, wherein HCl is absorbed from a further HCl-containing gas stream to form a second aqueous HCl solution.

9. The method according to claim 1, wherein the HCl-containing gas stream comprises one or more organic contaminants selected from the group consisting of acetic acid, monochloroacetic acid, acetaldehyde, chloroacetaldehyde, and dichloroacetaldehyde.

10. The method for recovering HCl from a HCl containing gas stream comprising the steps of
    providing a HCl containing gas stream with a temperature of −20 to 25° C., which is obtained as a by-product of a hydrogenation step wherein a feed comprising monochloroacetic acid (MCA) and dichloroacetic acid (DCA) is reacted with hydrogen to form a HCl-containing gas stream and a product stream comprising MCA and a reduced amount of DCA,
    feeding the HCl containing gas stream to an adiabatic absorption unit where it is contacted with water as an absorbent, resulting in the formation of a top gas stream and an aqueous HCl product solution,
    providing steam to the adiabatic absorption unit to maintain the temperature of the top gas stream to be at least 70° C. and wherein the amount of water is selected such that the aqueous HCl product solution has a HCl concentration in the range of 5-20 wt. %,
    diluting the aqueous HCl product solution to a concentration of 1-8 wt. %, and
    providing the diluted solution as absorbent in a second absorption step, wherein HCl is absorbed from a further HCl-containing gas stream to form a second aqueous HCl solution, which further HCl-containing gas stream is obtained as a by-product of a chlorination step wherein acetic acid is reacted with chlorine resulting in the formation of the second HCl-containing gas stream and a feed comprising monochloroacetic acid (MCA) and dichloroacetic acid (DCA).

11. The method of claim 10, wherein the HCl concentration in the absorbent water is below 0.5 wt. %.

12. The method of claim 10, wherein the steam added to the adiabatic absorption unit has a temperature of 100-200° C. and a pressure of 1 to 4 bar (absolute).

13. The method of claim 10, wherein the top gas stream has a temperature of at least 87° C. and at most 92° C.

14. The method of claim 10, wherein the temperature of the HCl-containing gas stream provided to the absorption unit is in the range of 10 to 15° C.

15. The method of claim 10, wherein the aqueous HCl product solution has a HCl concentration in the range of 13-18 wt. %.

\* \* \* \* \*